(12) United States Patent
Konings

(10) Patent No.: US 6,236,879 B1
(45) Date of Patent: May 22, 2001

(54) FIBER OPTIC CATHETER SYSTEM

(75) Inventor: Maurita Karel Konings, Utrecht (NL)

(73) Assignee: Centrum RRN Academisch Ziekenhuis Utrecht, Utrecht (NL)

( * ) Notice: Subject to any disclaimer, the term of this patent is extended or adjusted under 35 U.S.C. 154(b) by 0 days.

(21) Appl. No.: 09/155,333
(22) PCT Filed: Jan. 22, 1998
(86) PCT No.: PCT/NL98/00043
  § 371 Date: Nov. 24, 1998
  § 102(e) Date: Nov. 24, 1998
(87) PCT Pub. No.: WO98/32369
  PCT Pub. Date: Jul. 30, 1998

(30) Foreign Application Priority Data

Jan. 23, 1997 (NL) .................................................. 1005068

(51) Int. Cl.[7] .................................................. A61B 5/05
(52) U.S. Cl. ............................ 600/424; 606/15; 600/478
(58) Field of Search .................................. 600/424, 476, 600/478, 342, 117; 128/897, 899; 356/364, 370, 138, 152.1–153.3, 375; 385/115–117; 606/15, 16

(56) References Cited

U.S. PATENT DOCUMENTS 4,846,154 * 7/1989 MacAnally et al. ................. 385/117
5,515,864   5/1996 Zuckerman .
5,669,878 * 9/1997 Dickinson et al. .................... 604/95
5,769,843 * 6/1998 Abela et al. ........................... 606/15
5,833,605 * 11/1998 Shah ................................... 600/117

FOREIGN PATENT DOCUMENTS 0 347 140   12/1989 (EP) .
0 586 162    3/1994 (EP) .

* cited by examiner

Primary Examiner—Ruth S. Smith
(74) Attorney, Agent, or Firm—Darby & Darby

(57) ABSTRACT

A catheter system including a catheter having a proximal end and a distal end and a device for determining the position of the distal end of the catheter relative to the position of the proximal end of the catheter, the device for determining the position including a glass fiber within a lumen of the catheter, the lumen being defined by a wall, a first polarization filter near the proximal end of the catheter, and a second polarization filter near the distal end of the catheter, wherein the first and second polarization filters are fixed with respect to the wall, and wherein the glass fiber is suitable for transporting polarized light while maintaining the direction of the polarization of the light substantially unchanged during torsional stress of the catheter.

6 Claims, 2 Drawing Sheets

FIBER OPTIC CATHETER SYSTEM

FIELD OF THE INVENTION

The invention relates to a catheter system comprising a catheter having a proximal and a distal end and provided with means for determining the position of the distal end-of the catheter.

BACKGROUND OF THE INVENTION

Such a catheter has been described in applicant's Dutch patent application 1003033. The catheter described in said patent application is used as inner catheter fitted inside a guide catheter. The guide catheter is provided with first signal transmission means and the inner catheter is provided with second signal transmission means, which all extend between the proximal end and the distal end of the catheter system. At the distal end the first and second signal transmission means connect to each other in order to allow signal transmission to take place between the first and the second signal transmission means. The object of this system is to make it possible to determine the position of the inner catheter.

The aim of both the present invention and the above-mentioned Dutch patent application 1003033 is to solve the problem of there being no fixed relation between the angular position of the distal end of the catheter, that is the end of the catheter which is inside the patient, and the angular position of the proximal end of the catheter, where the catheter is controlled by rotation. It is therefore the objective of the invention to provide a catheter with which it is possible to reliably measure the angular position of the distal end.

To realize this, various proposals are already known from the prior art. The thesis "Scanning mechanisms for intravascular ultrasound imaging: a flexible approach" by H. ten Hof, 1993, ISBN 90-9006072-3, pp 120, 121, suggests as possibility an acoustic method applying acoustic measuring means which are placed in a perimeter and at a distance from each other, together with a noise source at the distal end of the catheter. Mention is also made of a capacitive measuring method wherein, dependent on the rotation of the catheter, a capacity adjustment of a capa city at the distal end takes place. A further suggestion is an electromagnetic method, wherein a micromotor is placed at the distal end for the adjustment of the catheter tip. Also mentioned is an optical reflection method wherein a code disc is used, provided with reflection lines, and positioned at the distal end of the catheter. However, all these known embodiments have proven to be unpractical, unworkable, or ineffective.

DE-A-3,435,369 does not relate to a catheter system but to an endoscope equipped with a polarization filter. The polarization filter serves to vary the illumination of an object to be observed with the aid of the endoscope such as to avoid over-adjustment of the video installation. The system disclosed in this publication is not equipped for the determination of the position of the catheter's distal end.

SUMMARY OF THE INVENTION

According to the invention a catheter system is proposed comprising a glass fiber incorporated in a lumen of the catheter, which lumen is defined by a wall, with a first polarization filter being provided near the proximal end of the catheter and a second polarization filter near the distal end of the catheter, which polarization filters are fixed with respect to the catheter wall, and which glass fiber is suitable for the transport of polarized light while in essence maintaining the direction of polarization of said light during torsional stress of the patheter. The polarization direction always relates to a fixed co-ordinate system which is invariant with respect to the catheter's torsion. By this very simple measure a catheter is provided requiring only a very small diameter, while nevertheless allowing direct determination of the angle position of the distal end.

In order for the light in respect of the polarization direction to be independent of the catheter's torsional stress, it is desirable that the structure of the glass fiber be circularly symmetrical. A suitable choice for a glass fiber with this quality is an embodiment with a glass fiber of the graded-index type.

The catheter system according to the invention may be provided with means, which are known in themselves for taking a measurement or for treating the respective part of the patient's body, and in which according to the invention a light source is applied to feed the glass fiber in the catheter. Said light is polarized by the first polarization filter provided near the proximal end of the catheter, is conducted further through the glass fiber in the catheter while maintaining the polarization direction of the polarized light and, depending on the adjustment of the second polarization filter with respect to the first polarization filter, is to a greater or lesser degree weakened through the second polarization filter positioned near the distal end of the catheter. The degree of weakening can be measured and serves as indication for the position of the distal end of the catheter in relation to the proximal end.

It is desirable that means are provided for the return transport of the light exiting at the distal end, from the second polarization filter. In this way the catheter may still be equipped very simply, while the costly measuring device is placed permanently in the catheter system at the proximal end of the catheter.

A very simple but effective form of this system is one in which a mirror is placed at the distal side of the second polarization filter, for the reflection of light exiting from the second polarization filter in the direction of the first polarization filter. The reflected light is able to pass through the second polarization filter unhindered and is subsequently returned to the proximal side where, due to the first polarization filter, a further weakening of the light may occur. At this proximal end the remaining light intensity can be measured to derive the angle position of the distal end of the catheter.

An alternative embodiment of the catheter system according to the invention is characterized in that at the distal side of the second polarization filter a return glass fiber is connected which is provided in the catheter's lumen and which exits at its proximal end.

The invention also relates to a separate catheter having a lumen defined by a wall, which lumen is characterized in that a glass fiber is incorporated in the lumen, extending between a proximal end and a distal end of the catheter and wherein at the proximal end a first polarization filter is provided and at the distal end a second polarization filter is provided, which polarization filters are fixed with respect to the catheter wall, and which glass fiber is suitable for the transport of polarized light while in essence maintaining the direction of polarization of said light during torsional stress of the catheter. With this catheter according to the invention, all elements determining the direction of polarization of the light to be fed through the glass fiber, including the first polarization filter, are integral parts of this catheter, so that apart from the driving device for the adjustment of the catheter at its proximal end, only the light source and the measuring means need to be outside of the catheter according to the invention.

The fixed connection of the polarization filters with respect to the catheter wall may be realised simply by gluing the polarization filters to the wall of the catheter.

BRIEF DESCRIPTION OF THE DRAWINGS

The invention will now be explained in more detail with reference to the drawing, in which.

DETAILED DESCRIPTION OF PREFERRED EMBODIMENTS

Figure 1:
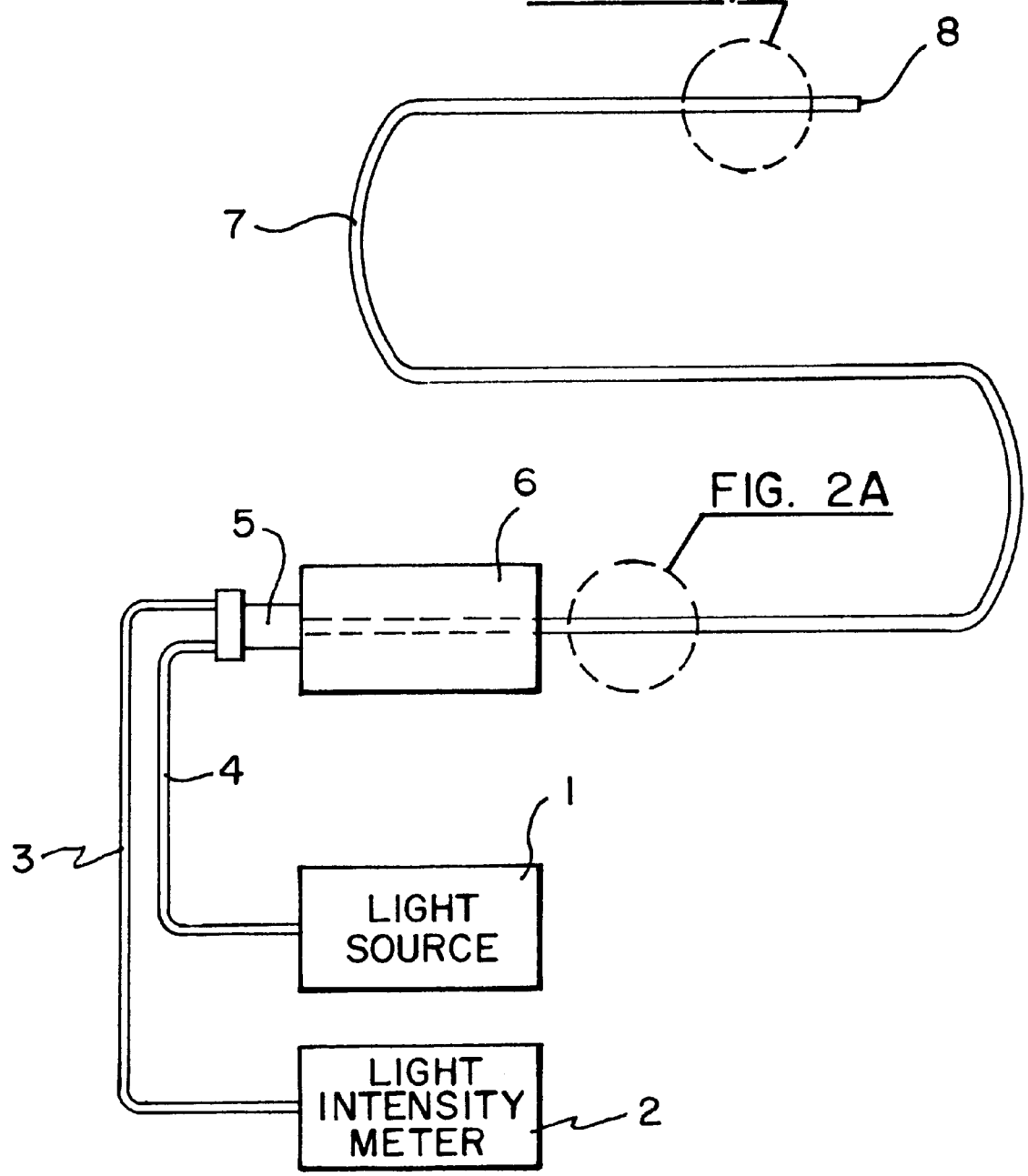
FIG. 1 shows the catheter system according to the invention, with the catheter according to the invention being part thereof.

Identical parts in the Figures are indicated by identical reference numbers.

It should be emphasized that the exemplified embodiment presented is not intended to be in any way limiting, and shows schematically how the system, respectively the catheter according to the invention, is equipped. Reference number 1 indicates a light source, for instance, a laser coupled via a glass fiber 4 with a connector 5 which couples the light signals through to the glass fiber 11 shown in FIG. 2A serving to feed the glass fiber in the catheter. The proximal end of the catheter is rotatingly driven by a driving motor 6. The catheter itself is indicated by reference number 7.

Figure 2A:
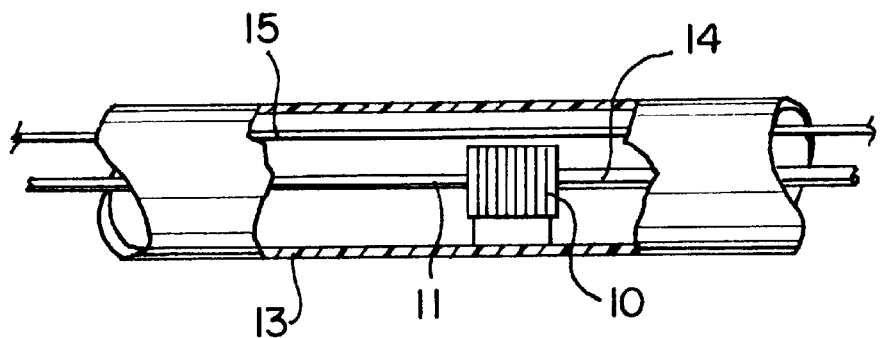
FIGS. 2A and 2B show longitudinal cross-sectional views of the catheter of FIG. 1, at two respectively labeled regions of the catheter of FIG. 1, in accordance with one embodiment of the invention.
Figure 2B:
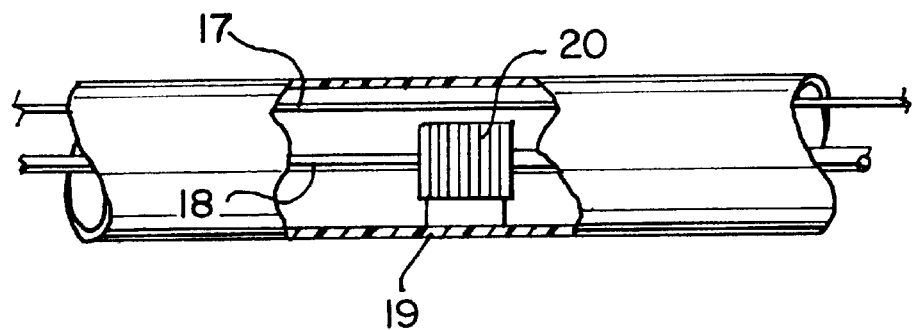

FIG. 2A, shows a first polarization filter 10 which has been fixed to the wall 13 of the catheter by means of a mechanical fixing agent, for instance, glue. Said wall 13, which in FIG. 2B (the distal end) is indicated by reference number 19, defines the lumen of the catheter in which a glass fiber 14 (near the proximal end) and 18 (near the distal end) is provided. This glass fiber serves for the transport of the polarized light while in essence maintaining the direction of polarization of said light during torsional stress of the catheter. The proximal end of the catheter 7 is fixed with respect to the driving motor 6. The first polarization filter may (as shown) be incorporated in the catheter according to the invention, or may be incorporated in a part located outside of the catheter and rotating with the proximal end of the catheter; for instance in the Figure to the right of driving motor 6. The second polarization filter 20, located near the distal end of the catheter 7, is also fixed to the wall 19 of the catheter by means of a mechanical fixing agent, such as glue.

Figure 3:
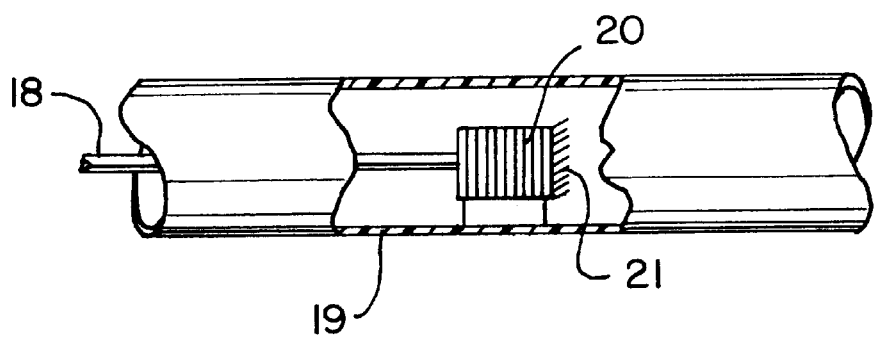
FIG. 3 shows a longitudinal cross-sectional view of the respectively labeled region in FIG. 1, in accordance with another embodiment of the invention.

The catheter system is further provided with a light intensity meter 2 (see FIG. 1). In order to be able to measure the light output at the distal side of the second polarization filter 20 by means of the light intensity meter 2 positioned at the proximal end, a first embodiment of the system according to the invention may be provided with a mirror 21 which may be positioned placed at the distal side of the second polarization filter. This is shown in FIG. 3. The embodiment shown is provided at the distal side of the second polarization filter 20 with a connected return glass fiber 17, which near the proximal end of the catheter is indicated by reference number 15. Via the connector 5, said return glass fiber is connected to glass fiber 3, which transports the returned light back to the light intensity meter 2. The light-intensity measurement can then be used to determine the angle position of the distal end of the catheter 7. The FIGURES. do not show that the glass fiber has a circle-symmetrical structure. This structure of glass fibers is in itself known to the person skilled in the art. Preferably the glass fiber is of the graded-index type.

Within the scope of the invention various embodiments are possible which are all based on the idea of the invention as specified in the appended claims. For instance, a separate catheter is also subject matter of the invention, in which the first polarization filter 10 and the second polarization filter 20 are located in the lumen of the catheter, fixed with respect to the catheter wall, and in which the glass fiber extends between the first polarization filter 10 and the second polarization filter 20, which glass fiber is suitable for the transport of polarized light while in essence maintaining the direction of polarization of said light during torsional stress of the catheter.

What is claimed is:

1. A catheter system comprising a catheter having a proximal end and a distal end and means for determining the position of the distal end of the catheter relative to the position of the proximal end of the catheter, said means for determining the position comprising a glass fiber within a lumen of the catheter, said lumen being defined by a wall, a first polarization filter near the proximal end of the catheter, and a second polarization filter near the distal end of the catheter, wherein said first and second polarization filters are fixed with respect to said wall, and wherein said glass fiber is suitable for transporting polarized light while maintaining the direction of polarization of said light substantially unchanged during torsional stress of the catheter.

2. A catheter system according to claim 1, wherein said means for determining the position further comprise means for return transport of light exiting from a distal side of said second polarization filter.

3. A catheter system according to claim 1, wherein said means for determining the position further comprise a mirror at a distal side of the second polarization filter which mirror reflects light exiting the second polarization filter in the direction of the first polarization filter.

4. A catheter system according to claim 1, comprising a return glass fiber connected to a distal side of the second polarization filter and extending within said lumen to proximal end of the catheter.

5. A catheter system according to claim 1 wherein the glass fiber has a circularly symmetrical structure.

6. A catheter system according to claim 1, wherein the glass fiber is of the graded-index type.

* * * * *

UNITED STATES PATENT AND TRADEMARK OFFICE
CERTIFICATE OF CORRECTION

PATENT NO. : 6,236,879 B1
DATED : May 22, 2001
INVENTOR(S) : Maurits Karel Konings Page 1 of 1

It is certified that error appears in the above-identified patent and that said Letters Patent is hereby corrected as shown below:

Title page,
Item [75] Inventor, change "Maurita Karel Konings" to -- Maurits Karel Konings --.

Signed and Sealed this

Twenty-ninth Day of January, 2002

Attest:

Attesting Officer

JAMES E. ROGAN
*Director of the United States Patent and Trademark Office*